McLachlan et al.

[11] Patent Number: 4,643,573
[45] Date of Patent: Feb. 17, 1987

[54] METHOD FOR MEASURING THE RELATIVE CONCENTRATION OF LARGER AND SMALLER PARTICLES IN SUSPENSION

[75] Inventors: Richard D. McLachlan; Ray W. Chrisman, both of Midland, Mich.

[73] Assignee: The Dow Chemical Company, Midland, Mich.

[21] Appl. No.: 703,796

[22] Filed: Feb. 21, 1985

[51] Int. Cl.$^4$ ............................................. G01N 21/49
[52] U.S. Cl. ...................................... 356/338; 356/342
[58] Field of Search ....................... 356/336, 338, 342; 250/564

[56] References Cited

U.S. PATENT DOCUMENTS 3,714,444 1/1973 Carr et al. ........................ 356/442 X
3,962,581 6/1976 Zimmerman ...................... 356/338 X

FOREIGN PATENT DOCUMENTS 0152444 11/1980 Japan ..................................... 356/441

Primary Examiner—David C. Nelms
Assistant Examiner—Matthew W. Koren

[57] ABSTRACT

The concentration of larger particles in a suspension of relatively small and relatively large light scattering particles is determined by illuminating a zone of the suspension with light of such wavelength as to be scattered more efficiently by the larger particles than by the smaller particles. The scattered light is collected and its intensity measured. The value of the collected light intensity then is compared with the corresponding value of the same wavelength light scattered by corresponding suspensions containing known concentrations of particles.

17 Claims, 3 Drawing Figures

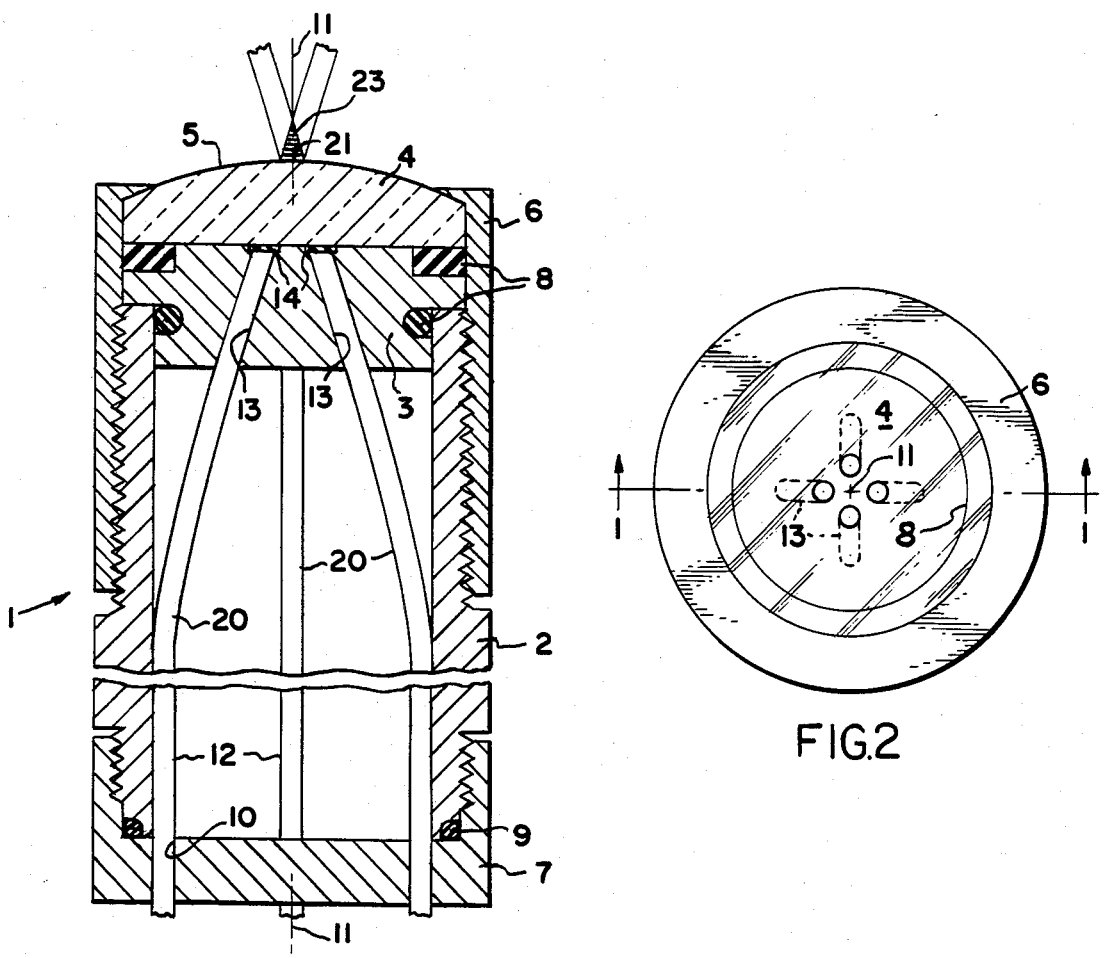
FIG.1
FIG.2
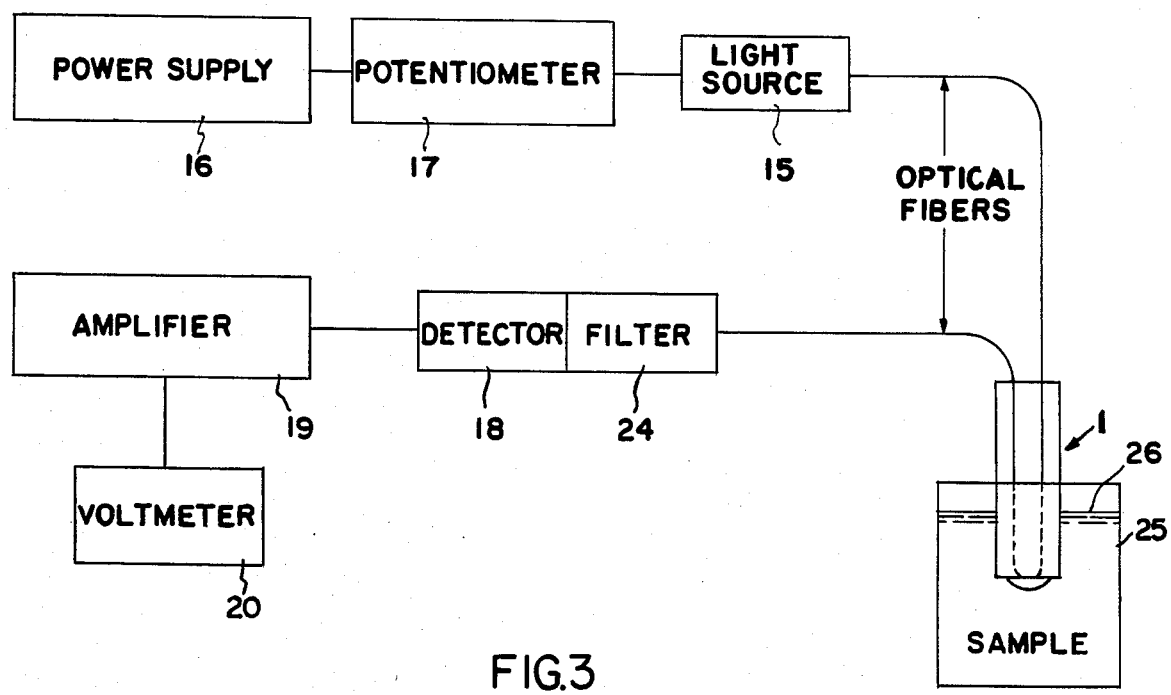
FIG.3

METHOD FOR MEASURING THE RELATIVE CONCENTRATION OF LARGER AND SMALLER PARTICLES IN SUSPENSION

This invention relates to a method for measuring the relative concentration of larger and smaller particles in suspension in a fluid medium and more particularly to a method wherein the relative concentration is determined by measuring the intensity of light scattered by the larger of such particles.

BACKGROUND OF THE INVENTION

In the manufacture of various products from fluid mediums containing essentially particles of two substantially different sizes in suspension, the desired physical properties of such products often depend upon the relative concentrations or proportions of the different size particles. For example, the physical and chemical properties of some latex products depend upon an optimum distribution of two groups of different diameter particles. Thus, the manufacture of one latex product having the desired characteristics will require the maintenance of one ratio between the smaller and the larger particles, whereas the manufacture of another latex product having different characteristics will require the maintenance of a quite different ratio between the larger and smaller particles. To produce products having the desired characteristics, therefore, it is necessary to determine the relative concentrations of the large and small particles.

One reliable technique currently in use for the determination of particle size distribution in suspensions involves the analysis of a suspension by hydrodynamic chromatography (HDC). Although the use of HDC in analyzing a suspension yields accurate, reliable data, the HDC apparatus is of such sophistication that its proper operation requires the services of a chemist or engineer. Further, HDC apparatus reveals considerably more information about a suspension than is required merely to determine the relative concentrations of two particle sizes. Consequently, the use of HDC apparatus for concentration analysis is not the most efficient use of such apparatus.

The analysis of a suspension using HDC apparatus often requires as much as twenty minutes' time to complete. Some production processes, however, require a more rapid method of analysis for process control. Further, it often occurs that HDC apparatus or personnel capable of operating it may not be available at the time an analysis of a suspension is desirable. As a consequence, it is not uncommon for the analysis of a suspension to be completed only after the process has been completed. In some instances, therefore, a finished product may not conform to specifications and must be discarded.

An object of the present invention is to provide a method of analyzing a fluid medium to determine the relative concentration of relatively large and relatively small particles in suspension in such medium and which is simple to perform, requires only a short time to complete, and utilizes relatively inexpensive equipment.

SUMMARY OF THE INVENTION

A method according to a preferred embodiment of the invention comprises illuminating each of a number of samples taken from a corresponding number of fluid mediums containing essentially two sizes of particles in suspension, one of which is relatively small and the other of which is relatively large. The relative concentration of the larger particles in each sample is known and the proportion of the larger particles of each sample is different. The composition of each medium is alike except for the differences in relative concentration of the respective particles. Each sample is illuminated with light which is of such wavelength as to be scattered much more efficiently by the larger particles than by the smaller particles. Light scattered by each sample is collected and its intensity measured, thereby establishing for each sample a value that is directly related to the proportion of the larger particles in such sample.

The same procedure then is repeated for a sample of a medium whose relative concentration of larger and smaller particles is to be determined. Such medium corresponds to those referred to earlier with the exception that the relative concentration of the particles is not known. The intensity of the light scattered by the particles of the sample under analysis may be the same as or different from the light scattered by the larger particles of the preceding samples. If the intensities are the same, then the relative concentrations of the particles are the same. If the intensities are different, the relative concentrations of the particles of the sample under analysis may be determined by comparison with data obtained from the samples having known relative concentration of particles.

The determination of relative concentrations according to the invention is rapid, thereby enabling corrective action, if needed or desirable, to be taken with respect to a batch of material undergoing processing.

THE DRAWING

Apparatus for use in performing the method according to the invention is disclosed in the accompanying drawing wherein:

FIG. 1 is a fragmentary, vertical sectional view taken on the line 1—1 of FIG. 2 and illustrating a suitable illuminating and scattered light collecting probe;

FIG. 2 is a top plan view of the probe; and

FIG. 3 is a diagrammatic view of additional apparatus used with the probe in performing the method.

DETAILED DESCRIPTION

The method according to the invention effects the measurement of the relative concentrations of particles in suspension in a fluid medium containing essentially two different sizes of particles. The method is particularly useful in analyzing latex mediums, but is useful with other mediums of primarily dual size particle population.

The method according to the invention relies upon the phenomenon that, when a suspension of small diameter particles is illuminated with light of a wavelength larger than the particle diameter, the intensity of light scattered by such particles depends on the ratio of the wavelength to the particle diameter and varies inversely with particle diameter if the wavelength is constant. If particles of two different sizes are present in the same suspension, the intensity of the scattered light is the sum of that scattered by the larger and the smaller particles. If the total concentration of particles (i.e., weight fraction) is fixed, the total intensity of the scattered light will increase with increasing relative concentration (i.e., proportion) of the larger particles due to the fact that the larger particles scatter light more efficiently than the smaller particles. For example, if a suspension having a fixed weight fraction of particles whose diameters are 0.1 micron and 0.5 micron is illuminated with light having a wavelength of 1 micron (or any wavelength greater than 0.5 micron) the intensity of the scattered light will increase with an increase in the proportion of 0.5 micron particles in the suspension.

The difference between diameters of the two groups of particles need not conform to a rigid standard. In general, the larger the difference, within reasonable limits, the better the method performs. Thus, a ratio range of between about 2 to 1 and 10 to 1 between the diameters of the larger and smaller particles enables satisfactory results to be achieved.

Apparatus adapted for use in performing the method according to the invention comprises a fiber optic probe 1 for illuminating a sample of a fluid medium containing particles in suspension and collecting light scattered by such particles. The probe may correspond to one or more of those disclosed in copending application Ser. No. 678,115, filed Dec. 4, 1984, and to which reference may be had for a detailed disclosure. Briefly, however, the probe 1 has a tubular body 2 formed of suitable metallic or other material appropriate for immersion in a sample of a fluid medium that is to be examined. At one end of the body 2 is a support 3 and a transparent window 4 formed of suitable material, such as glass, quartz, sapphire, and the like. The window preferably has a convex outer surface 5 and is maintained in assembled relation with other parts of the probe by means of a flanged cap 6 threaded onto one end of the body 2. The opposite end of the body 2 accommodates a cap 7. The probe is equipped with suitable seals 8 and 9 at its opposite ends.

The cap 7 is provided with two or more, and preferably four, axially extending openings 10 which are radially and circumferentially spaced at uniform distances about the longitudinal axis 11 of the body 2. Extending through each of the openings 10 is an optical fiber 12 of preferably uniform diameter. The fibers extend through the body 2 and have corresponding ends fixed in openings 13 formed in the support 3. The openings 13 also are radially and circumferentially spaced uniformly about the axis 11 of the probe, but unlike the openings 10, the openings 13 converge in a direction toward the window end of the probe. The fibers 12 extend through the openings 13 and abut the inner surface of the window. Preferably, a thin coating 14 of an optical coupling gel or oil having a refractive index similar to that of the fibers and the window is interposed between the window and the confronting ends of the fibers to reduce reflection losses at the fiber/window interface.

At least one of the fibers 12 is coupled to a light source 15 that communicates with a D.C. power supply 16 via a potentiometer 17. Such fibers hereinafter will be referred to as illuminating fibers. One or more of the remaining fibers, hereinafter referred to as light collecting fibers, are coupled to a light detector 18, an amplifier 19, and a voltmeter 20 for purposes to be explained in more detail hereinafter. For the time being, however, it is sufficient to state that the longitudinal axes of all of the fibers 12 intersect one another and the longitudinal axis of the probe 1 at a common point 21 which lies on the outer surface of the window 4.

Light transmitted by each illuminating fiber passes through and beyond the window as a substantially conical beam. The diameter of each of the light collecting fibers preferably corresponds to that of the illuminating fiber. The light from each illuminating fiber will illuminate a zone or region of the medium and the extension of the diameter of each light collecting fiber will intersect each illuminated zone and form fields of view originating at the outer surface 5 of the window 4. A field of view is indicated at 23 in FIG. 1.

If more than one illuminating fiber is used, they should be diametrically opposed to one another to avoid causing reflections from the window falling on the light collecting fibers. For convenience of illustration only one illuminating fiber and one light collecting fiber are shown in FIG. 3.

A suitable monochromatic light source is a Math Associates Model E-1520 GaAs light emitting diode (LED) which emits light at a wavelength at least as great as the diameter of the larger particles in suspension. The light source, however, may be polychromatic if desired. A suitable detector is a United Detector Technology (UDT) Model 6DP PIN silicon diode detector. A suitable amplifier is a UDT Model 101C transimpedance amplifier or any equivalent having a transimpedance gain of $10^6$ or $10^7$ V/A.

If a polychromatic light source is used, an optical filter 24 should be interposed between the collecting fiber and the detector 18 so as to exclude from the latter light having wavelengths other than a selected wavelength emitted from the light source.

To condition the apparatus for use, it first must be calibrated. The calibration procedure comprises obtaining a number, preferably three or more, of different calibration samples of fluid mediums corresponding to those which subsequently are to be examined, except that the concentration of the larger particles in each calibration sample is known. The concentration of the larger particles of each calibration sample should be different from the concentration of the particles of each other sample, thereby providing a number of calibration samples having a range of relative concentrations of particles.

One of the calibration samples is selected as the primary calibration sample. The sample so selected is one whose relative particle concentration approximates the desired relative particle concentration of the sample to be analyzed.

The voltage supplied from the power supply to the light source 15 is adjusted by means of the potentiometer 17 so that the current is between about 70% and 80% of the operating limit of the light source. The probe then is immersed in the primary calibrating sample. Particles in the field of view 23 will be illuminated and thus will cause some of the illuminating light to be scattered. Scattered light in the field of view will be collected by the collecting fiber or fibers and transmitted to the detector 18. The gain of the transimpedance amplifier 19 is adjusted to obtain a selected output as indicated by the voltmeter. This voltage is representative of the concentration of the larger particles in suspension and is recorded.

Without changing the voltage applied to the light source or the gain of the amplifier, the foregoing steps are repeated for each additional calibration sample, the probe being cleaned carefully between each measurement.

Following completion of the measurements and recordation of the voltages obtained with all of the calibration samples, computation of the mathematical constants (a) and (b) may be accomplished by the method of least square for the linear regression equation:

$$C = aV + b \quad \text{(Eq. 1)}$$

where C is the concentration of larger particles and V is the measured voltage. The concentration values computed for each calibration sample also may be plotted or charted.

When it is desired to examine a fluid medium corresponding to those of the calibrating samples, but wherein the relative concentration of the particles is unknown, a sample 26 is taken of the medium to be analyzed and placed in a suitable container 25, following which the probe is recalibrated by immersion in the primary calibration sample. If necessary, the potentiometer is adjusted to yield the same voltage previously obtained in the calibration step using the same primary calibration sample. Thereafter, the probe may be cleaned and immersed in the sample 26 of the medium to be analyzed. A voltage will be indicated on the voltmeter, and the value of such voltage may be inserted into Equation 1, thereby enabling the concentration of the larger particles to be calculated.

If the calculated concentration is more or less than that desired, the blend of larger and smaller particles in the batch of material undergoing processing may be adjusted, or other appropriate action taken.

If it could be assured that no changes would occur in the testing apparatus, recalibration of the probe prior to conducting each test would not be required. However, recalibration of the probe prior to examining a medium containing the unknown relative particle concentrations is desirable for several reasons. For example, the temperature of the probe or of the calibration sample may have changed, or the potentiometer may have been adjusted either deliberately or inadvertently. In any event, recalibration and calculation of the relative concentration of smaller and larger particles in a medium require no more than two or three minutes, at most. Thus, it is possible to monitor a batch of materials as they are being processed.

In the performance of the method according to the foregoing description the intensity of the illuminating light may be varied by adjustment of the potentiometer 17. It is possible, however, to apply a constant voltage to the light source and vary the gain of the amplifier 19. Alternatively, the voltmeter could be equipped with a potentiometer to vary the voltage supplied to it via the amplifier.

Once experience has been gained in practicing the method an operator will be able to compare the measured intensity of scattered light collected from a medium whose relative concentration of larger and smaller particles is unknown with the intensity of scattered light collected from a corresponding medium from which an acceptable substance has been produced, and thereby know whether any adjustment in the blend of the medium under analysis is required.

In this disclosure the term "light" has been used for convenience to refer to the radiant energy which illuminates the medium containing the particles. It is not intended to limit the frequencies of such radiant energy to those within the visible spectrum, however, inasmuch as radiations in the ultraviolet and infrared wavelengths beyond the visible spectrum may be utilized in the practice of the method.

What is claimed is:

1. A method for determining the relative concentration of relatively large and small light scattering particles in suspension in a fluid medium, said method comprising:
   (a) illuminating said medium with light of a wavelength that is scattered more efficiently by the larger particles than by the smaller particles;
   (b) collecting scattered light;
   (c) measuring the intensity of the collected scattered light; and
   (d) determining the concentration of the larger particles by comparing the intensity of scattered light with calibration values obtained by the application of steps (a), (b), and (c) to a like medium having in suspension correspondingly sized large and small particles of known concentration.

2. The method according to claim 1 wherein the illuminating light is substantially monochromatic.

3. The method according to claim 1 wherein the illuminating light is polychromatic.

4. The method according to claim 3 including filtering the collected scattered light and measuring the intensity of a selected wavelength of such scattered light.

5. The method according to claim 1 wherein the relatively large particles are of substantially uniform diameter.

6. The method according to claim 1 wherein the illuminating light has a wavelength at least as great as the diameter of the larger particles.

7. The method according to claim 1 wherein the illuminating light has a wavelength of between about 1 to 5 times the diameter of the larger particles.

8. The method according to claim 1 wherein the smaller particles are of substantially uniform diameter.

9. The method according to claim 1 wherein the larger particles are of substantially uniform diameter and the smaller particles are of substantially uniform diameter.

10. The method according to claim 9 wherein the ratio between the diameters of the larger and the smaller particles has a range of between about 2 to 1 and 10 to 1.

11. A method for determining if the relative concentration of larger and smaller light scattering particles in suspension in a fluid medium has an acceptable value for a substance to be produced from said suspension, said method comprising:
   (a) illuminating a zone of said suspension with light of such wavelength as to be scattered more efficiently by said larger particles than by the smaller particles;
   (b) collecting scattered light;
   (c) measuring the intensity of the collected scattered light; and
   (d) comparing the measured intensity of the collected scattered light with the intensity of light scattered by a corresponding suspension in a like fluid medium from which an acceptable like substance has been produced.

12. The method according to claim 11 wherein the illuminating light is substantially monochromatic.

13. The method according to claim 11 wherein the illuminating light is polychromatic.

14. The method according to claim 13 including filtering the collected scattered light and measuring the intensity of a selected wavelength of such scattered light.

15. The method according to claim 11 wherein the illuminating light has a wavelength at least as great as the diameter of the larger particles.

16. The method according to claim 11 wherein the larger particles are of substantially uniform diameter and the smaller particles are of substantially uniform diameter.

17. The method according to claim 11 wherein the ratio between the diameters of the larger and smaller particles has a range of between about 2 to 1 and 10 to 1.

* * * * *